US010596336B2

(12) United States Patent
Larsson et al.

(10) Patent No.: US 10,596,336 B2
(45) Date of Patent: Mar. 24, 2020

(54) NEURALLY TRIGGERED SUPPORT VENTILATION DURING HIGH FREQUENCY VENTILATION

(71) Applicant: MAQUET CRITICAL CARE AB, Solna (SE)

(72) Inventors: Ake Larsson, Jarfalla (SE); Mario Loncar, Ekero (SE); Erik Cardelius, Djursholm (SE)

(73) Assignee: Maquet Critical Care AB, Solna (SE)

(*) Notice: Subject to any disclaimer, the term of this patent is extended or adjusted under 35 U.S.C. 154(b) by 872 days.

(21) Appl. No.: 15/024,248

(22) PCT Filed: Sep. 24, 2014

(86) PCT No.: PCT/SE2014/051094
§ 371 (c)(1),
(2) Date: Mar. 24, 2016

(87) PCT Pub. No.: WO2015/047168
PCT Pub. Date: Apr. 2, 2015

(65) Prior Publication Data
US 2016/0228661 A1  Aug. 11, 2016

(30) Foreign Application Priority Data
Sep. 25, 2013 (SE) ...................... 1351106

(51) Int. Cl.
*A61M 16/00* (2006.01)
*A61B 5/00* (2006.01)
(Continued)

(52) U.S. Cl.
CPC ....... *A61M 16/0096* (2013.01); *A61B 5/0488* (2013.01); *A61B 5/0492* (2013.01);
(Continued)

(58) Field of Classification Search
CPC .......... A61M 16/0069; A61M 16/0096; A61M 16/12; A61M 2202/0208;
(Continued)

(56) References Cited

U.S. PATENT DOCUMENTS 5,165,398 A  11/1992 Bird
8,931,478 B2  1/2015 Dunsmore et al.
(Continued)

FOREIGN PATENT DOCUMENTS

EP  0 512 285 A1  11/1992
EP  1 106 197 A2  6/2001
(Continued)

*Primary Examiner* — Timothy A Stanis
*Assistant Examiner* — Matthew R Moon
(74) *Attorney, Agent, or Firm* — Schiff Hardin LLP

(57) ABSTRACT

A ventilation system provides patient-triggered support ventilation to a spontaneously breathing patient during ongoing high frequency ventilation (HFV), and has a pneumatic unit operated by a control computer for delivery of breathing gas in response to an effort to breathe by the patient, and an oscillator for superimposing high frequency oscillation onto the breathing gas. The system further includes a bioelectric sensor that measures a bioelectric signal indicative of the patient's efforts to breathe, and the control computer controls the delivery of breathing gas in response to the patient's effort to breathe, based on this bioelectric signal. The ventilation system is hence designed for neurally triggered support ventilation during ongoing HFV, which makes the trigger mechanism of the ventilation system more precise and robust compared to known trigger mechanisms of HFV ventilation systems.

10 Claims, 1 Drawing Sheet

(51) Int. Cl.
*A61B 5/0488* (2006.01)
*A61B 5/0492* (2006.01)
*A61M 16/12* (2006.01)

(52) U.S. Cl.
CPC .......... *A61B 5/4836* (2013.01); *A61B 5/6852* (2013.01); *A61M 16/0069* (2014.02); *A61M 16/12* (2013.01); *A61M 2202/0208* (2013.01); *A61M 2205/3303* (2013.01); *A61M 2205/3331* (2013.01); *A61M 2210/105* (2013.01); *A61M 2210/1014* (2013.01); *A61M 2210/1021* (2013.01); *A61M 2230/08* (2013.01); *A61M 2230/60* (2013.01)

(58) Field of Classification Search
CPC .. A61M 2205/3303; A61M 2205/3331; A61M 2210/1021; A61M 2210/105; A61M 2210/1014; A61M 2230/08; A61M 2230/60; A61B 5/0488; A61B 5/0492; A61B 5/4836; A61B 5/6852
See application file for complete search history.

(56) References Cited

U.S. PATENT DOCUMENTS

| | | | | |
|---|---|---|---|---|
| 2008/0200966 | A1* | 8/2008 | Blomberg | A61M 16/00 607/42 |
| 2009/0126731 | A1* | 5/2009 | Dunsmore | A61M 16/024 128/203.12 |
| 2009/0229612 | A1* | 9/2009 | Levi | A61M 16/0096 128/204.22 |
| 2010/0252038 | A1* | 10/2010 | Lagerborg | A61B 5/0488 128/204.23 |
| 2012/0103334 | A1* | 5/2012 | Sinderby | A61B 5/08 128/204.18 |
| 2013/0133655 | A1* | 5/2013 | Kimm | A61M 16/0057 128/204.23 |

FOREIGN PATENT DOCUMENTS

| | | |
|---|---|---|
| WO | WO-2006/037184 A1 | 4/2006 |
| WO | WO-2006/131149 A1 | 12/2006 |
| WO | WO-2011/073839 A2 | 6/2011 |

* cited by examiner

NEURALLY TRIGGERED SUPPORT VENTILATION DURING HIGH FREQUENCY VENTILATION

BACKGROUND OF THE INVENTION

Field of the Invention

The present invention relates to a ventilation system for providing patient-triggered ventilatory support to a spontaneously breathing patient during ongoing high frequency ventilation (HFV) of the patient.

Description of the Prior Art

HFV ventilators supply breathing gas to the airways of a patient via a patient circuit from a frequency of approximately 150 breaths per minute up to 900 breaths per minute or more, and with tidal volumes significantly less than required during spontaneous breathing, typically at or below anatomical dead-space volumes. This is in marked contrast to a conventional mechanical ventilator which typically supplies breathing gas to the patient circuit at a frequency and with a tidal volume close to the values during spontaneous breathing.

An HFV ventilator generally comprises an oscillator which is connectable in gas communication with one end of the gas tubing of a patient circuit. The circuit terminates in an opposite end, such as in an endotracheal tube, for connection to a patient's airways. The oscillator is then driven to vibrate a column of gas within the circuit to actively supply gas to and sometimes also to extract gas from the airways of the patient. Typically, the HFV ventilator comprises a gas supply for providing a constant, continuous so called 'bias' flow to the patient. This bias flow intersects the oscillatory pathway and serves to maintain (bias) a mean positive airway pressure about which the high frequency oscillations generated by the HFV ventilator occurs and also to wash exhaled gasses from the circuit. Gas leaves the circuit through an expiratory limb, which may be designed as a low pass filter. The bias supply of such systems is usually insufficient to supply sufficient gas to a patient if the patient should attempt a spontaneous breath.

One known patient ventilator system, which reduces this problem, is disclosed in U.S. Pat. No. 5,165,398. The system comprises an HFV ventilator and a conventional mechanical ventilator connected to a patient breathing circuit and cooperable to provide, in one mode of operation, a conventional low frequency, large tidal, volume time cycled mechanical ventilator supply having superimposed thereon high frequency oscillations from the HFV ventilator. In another mode of operation this system can act as an HFV ventilator with the conventional mechanical ventilator providing the continuous bias flow at a level to maintain a constant pressure. A mechanical pressure regulator is provided in the patient circuit proximal the patient end which operates to increase this continuous bias flow and maintain the pressure as a patient attempts to breathe spontaneously. A non-assisted spontaneous breathing support mode of operation is thereby provided.

EP 1106197 discloses an HFV ventilation system capable of providing assisted support of a spontaneous breathing effort detected during high frequency oscillation ventilation. This is achieved by monitoring changes in one or both of the gas pressure and gas flow during the operation of an HFV ventilator, which changes are unrelated to the high frequency oscillations produced by that ventilator. Thereby, a spontaneous breathing effort can be detected and a gas supply, preferably a conventional mechanical ventilator, can be operated to supply breathing gas at a level to assist the detected spontaneous breathing effort. When a spontaneous breathing effort by a patient is detected the high frequency oscillations are reduced or removed from the gas in the patient circuit, which switches the operating mode of the ventilation system from an operation mode of an HFV ventilator to an operation mode of a conventional mechanical ventilator.

The proposed combination of HFV and pneumatically (flow or pressure) triggered ventilation support may, in certain circumstances and in certain types of ventilation systems, have the disadvantage of being imprecise due to the difficulty of accurately identifying and measuring the changes in flow or pressure caused by the patient's effort to breathe within the high frequency pressure oscillations caused by the HFV ventilator. Furthermore, it requires time trend analysis of the monitored pressure or flow in order to minimize the risk of mistaking gas leakage or hyperinflation for spontaneous breathing attempts by the patient.

SUMMARY OF THE INVENTION

It is an object of the invention to provide an improved or at least alternative way of providing patient-triggered support ventilation to a spontaneously breathing patient during ongoing high frequency ventilation (HFV).

According to a first aspect of the invention there is hence provided a ventilation system for providing patient-triggered support ventilation to a spontaneously breathing patient during ongoing HFV, comprising:
  a pneumatic unit for delivery of breathing gas to the patient in response to an effort to breathe by the patient;
  a control unit for controlling the delivery of breathing gas by said pneumatic unit;
  an oscillator arrangement for superimposing high frequency oscillation onto said breathing gas;
  a bioelectric sensor arrangement configured to measure a bioelectric signal indicative of the patient's efforts to breathe,
  the control unit being configured to control the delivery of breathing gas in response to the patient's effort to breathe, based on said bioelectric signal.

That the delivery of breathing gas to the patient during ongoing HFV is controlled based on a bioelectric signal indicative of the patient's effort to breathe means that the ventilation system according to the invention is configured to provide a novel type of ventilation mode combining HFV and neurally triggered support ventilation, hereinafter referred to as HFNAVA. This is in contrast to known ventilation systems for providing patient-triggered support ventilation during ongoing HFV, all of which are pneumatically triggered based on changes in a monitored pressure or flow.

Using neural triggering of gas delivery during ongoing HFV is advantageous compared to using pneumatic triggering since it is sometimes hard to distinguish flow or pressure changes caused by the patient's effort to breathe from flow or pressure changes caused by the ongoing HFV. Since the bioelectric signal used for triggering gas delivery in the ventilation system according to the invention is independent of the high frequency pressure oscillations induced by the HFV, a more precise and robust way of providing accurate support ventilation during ongoing HFV is provided.

Preferably, the bioelectric signal is an electromyographic (EMG) signal and the bioelectric sensor arrangement is an EMG detector, such as an oesophageal catheter well known in the art, configured to measure an EMG signal from the diaphragm of the patient.

In one embodiment of the invention, the ventilation system comprises a ventilator configured to provide neurally adjusted ventilatory assist (NAVA) by controlling the delivery of breathing gas to the patient based on EMG signals detected by said EMG detector. The oscillator arrangement for superimposing high frequency oscillation onto the breathing gas may be integrated in the NAVA-enabled ventilator or be an external oscillation unit that is connected in gaseous communication with an inspiration line or a common line of a patient circuit connecting the ventilator with the patient.

In another embodiment, the ventilation system comprises a ventilator particularly adapted to provide HFV (i.e. high frequency, small tidal breaths) to a patient, the HFV-enabled ventilator being modified so as to also be able to supply low frequency, large tidal breaths to the patient in response to a monitored bioelectric signal indicative of the patient's effort to inhale, wherein the high frequency oscillation of the HFV is superimposed onto the low frequency, large tidal breaths.

The ventilation system according to the invention may hence be configured to combine HFV and NAVA (Neurally Adjusted Ventilatory Assist) in a ventilation mode that is herein referred to as HFNAVA. In this mode, breathing gas is supplied to the patient according to a pressure profile that is determined based on EMG-signals indicative of the patient's own breathing efforts, and high frequency pressure oscillations are superimposed onto that pressure profile.

Preferably, the control unit of the ventilation system is configured to control both the pneumatic unit delivering the normal breaths to the patient in response to the patient's effort to breathe, and the oscillator arrangement that superimposes the high frequency oscillation onto the normal breaths. In this context, "normal breaths" are breaths that are provided at much lower frequency and with much larger tidal volumes than the high frequency, small tidal breaths delivered by the oscillator arrangement. The delivery frequency (i.e. the respiratory rate) and the tidal volume of said normal breaths are controlled by the control unit to fulfil the respiratory needs of the patient, as indicated by the measured bioelectric signals (EMG signals), meaning that the pneumatic unit delivers breaths that are in synchrony with and proportionate to the patient's efforts to breathe.

The effect of the control unit being able to control both the delivery of normal breaths and the high frequency oscillation is that they can be controlled in relation to each other in a manner making the overall ventilation of the patient fulfil the respiratory needs of the patient, as indicated by the bioelectric signals. Yet another effect is that the control unit can control the ventilation system to switch between different modes of ventilation, including but not limited to NAVA (EMG controlled ventilation), HFV, and HFNAVA.

Further advantageous aspects of the invention will be described in the detailed description following hereinafter.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DESCRIPTION OF THE PREFERRED EMBODIMENTS

Figure 1:
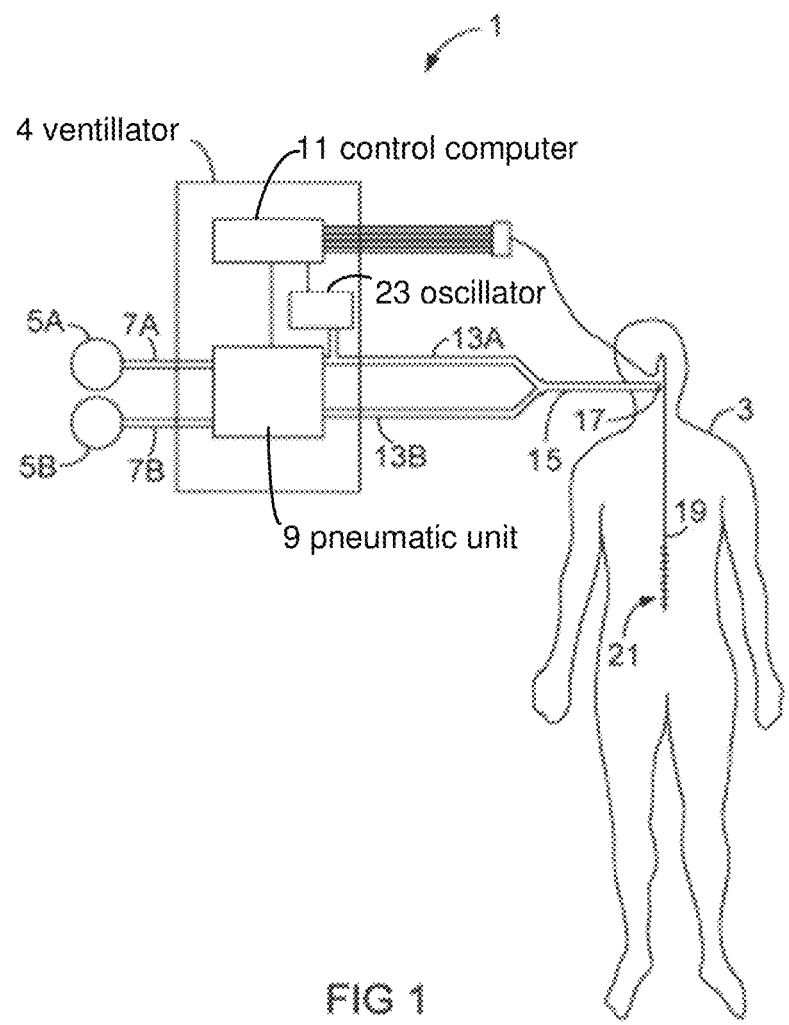
FIG. 1 illustrates a ventilation system for providing combined patient-triggered support ventilation and HFO ventilation to a patient, according to an exemplary embodiment of the invention.

The present invention strives to solve the problem of how to provide patient-triggered support ventilation to a spontaneously breathing patient during ongoing high frequency ventilation (HFV). As described above, HFV is a ventilation mode in which very small tidal volumes are delivered at high frequency, typically in the frequency range of 5 to 20 Hz. The rapidly fluctuating pressure in HFV systems makes it difficult to implement precise and robust pneumatic triggering of the support ventilation.

Relevant parameters defining the characteristics of the HFO ventilation include MAP (mean airway pressure), the oscillation frequency and the amplitudes of the oscillating pressure profile. As well known in the art, there are several subcategories of HFV. One subcategory of HFV is high frequency oscillatory ventilation (HFOV), sometimes also referred to as active high frequency ventilation (HFV-A). In HFOV, the oscillating pressure profile applied to the patient oscillates between a positive and a negative pressure in relation to surrounding pressure (atmospheric pressure), which makes both inspiration and expiration "active" and so minimizes the risk of gas trapping in the patient. It should be appreciated that HFV in the context of this application is not limited to any particular type of HFV, and so includes also HFOV.

The problem of how to provide precise and robust support ventilation to a spontaneously breathing patient undergoing HFV is solved by the present invention by providing a ventilation system capable of providing HFV in combination with neurally triggered support ventilation.

In one exemplary embodiment of the invention, which will be described below, the ventilation system is configured to be operated in a ventilation mode combining HFV and neurally adjusted ventilatory assist (NAVA), the latter sometimes being referred to as EMG controlled ventilation.

The act of taking a breath is controlled by the respiratory center of the brain, which decides the characteristics of each breath, timing and size. The respiratory centre sends a signal along the phrenic nerve, excites the diaphragm muscle cells, leading to muscle contraction and descent of the diaphragm dome. As a result, the pressure in the airway drops, causing an inflow of air into the lungs.

NAVA is a mode of mechanical ventilation in which the electrical activity of the diaphragm (Edi) is captured, fed to the NAVA-enabled ventilator and used to assist the patient's breathing in synchrony with and in proportion to the patient's own efforts. As the ventilator and the diaphragm work with the same signal, mechanical coupling between the diaphragm and the ventilator is practically instantaneous.

In NAVA, the patient's breathing efforts are typically sensed by measuring the electromyogram (EMG) of the contracting diaphragm. EMG signals are typically measured by means of an oesophageal catheter comprising an array of electrodes. The EMG signals are then processed in various ways and a signal representative of the Edi is calculated. The supply of gas from the ventilator to the patient is then controlled in a suitable manner in synchrony with and in proportion to the Edi.

Various aspects of the NAVA technology are described in e.g. WO 1998/48877, WO 1999/62580, WO 2006/131149, and WO 2008/131798.

FIG. 1 illustrates a ventilation system 1 for providing neurally triggered support ventilation to a patient 3 during ongoing HFV, according to an exemplary embodiment of the invention.

The ventilation system 1 comprises a ventilator 4 that can be connected to one or more gas sources 5A, 5B through one or more gas connections 7A, 7B. For example, the breathing apparatus may be connected to a first gas source for the supply of pressurised air and a second gas source for the supply of pressurised oxygen. The flows of gases from the gas sources 5A, 5B are mixed and regulated to a breathing gas in a pneumatic unit 9 that is controlled by a control computer 11 of the ventilator 4. The pneumatic unit 9 may, among other things, include valves that are controlled by the control computer 11 in order to regulate the composition, pressure and flow of the breathing gas delivered to the patient 3. To this end, the control computer 11 may utilize feedback data from various sensors (not shown), such as gas analyzers, flow sensors and pressure gauges, arranged within the ventilator 4 or elsewhere in the ventilation system 1.

The breathing gas is then led from the ventilator 4 to the patient 3 through a tubing system often referred to as patient circuit. The patient circuit has an inspiratory line 13A conveying breathing gas to the patient 3, an expiratory line 13B conveying exhaled gases away from the patient, a common line 17 connected to the inspiratory and expiratory lines via a Y-piece, and a patient connector 17, e.g. in form of a breathing mask or a tracheal tube, connecting the common line 17 with the airways of the patient 3. Using an invasive patient connector, such as a tracheal tube, is advantageous compared to using a non-invasive patient connector, such as a breathing mask, since leakage in non-invasive patient connectors tends to reduce the pressure oscillations of the HFV ventilation.

The ventilation system 1 further has a bioelectric sensor 24 connected to the control computer 11 of the ventilator 4 and configured to detect bioelectric signals indicative of the patient's efforts to breathe. In this embodiment, the bioelectric sensor 24 is an EMG detector that is realized in form of an oesophageal catheter 19 configured to record a myoelectrical signal (EMG signal) from the diaphragm of the patient 3. The catheter 19 comprises a number of electrodes 23, for example nine electrodes placed equidistantly from each other in an array along the catheter 19 to produce eight subsignals, each subsignal being a difference signal between two adjacent electrodes. The subsignals are processed by the control computer 11 to calculate a signal, the Edi signal, representing the electrical activity of the diaphragm and so indicative of the patient's efforts to breathe. The Edi signal is then used by the control computer 11 to control the supply of breathing gas to the patient 3 in synchrony and proportion to the patient's own efforts to breathe.

Although exemplified in form of an oesophageal catheter 19, the bioelectric sensor 24 could be any known detector arrangement for detecting EMG signals or other bioelectric ventilation related signals. For example, the bioelectric sensor 24 could include surface electrodes placed on the ribcage, the abdomen or in the vicinity of the phrenic nerve to sense and filter out EMG signals. The bioelectric sensor 24 could also have one or more electrodes for measuring muscular activity related to the patient's breathing other than the muscular activity of the diaphragm.

In dependence of the EMG signal received from the oesophageal catheter 19, the control computer 11 generates a control signal that is emitted as a control signal to the pneumatic unit 9. In this way, the pneumatic unit 9 is controlled in dependence of EMG signals obtained from the patient. The principles of such control are further described in e.g. WO 1998/48877 and WO 1999/62580.

As long as the ventilation system 1 uses the EMG signals as control parameter for the supply of breathing gas, the breathing will follow the natural breathing cycles that are ultimately determined by the patient's breathing center, which in turn constitutes a direct indicator of the patient's actual breathing needs.

The ventilation system 1 further has a high frequency oscillator 23, hereinafter referred to as an oscillator, for providing high frequency ventilation (HFV) to the patient 3. The oscillator 23 may form an integral part of the ventilator 4, or it may be arranged external to the ventilator 4 to form a separate oscillator unit arranged within or in gaseous communication with the inspiration line 13A or the common line 15.

In the embodiment illustrated in FIG. 1, the oscillator 23 is integrated in the ventilator 4. As shown in FIG. 1, the integrated oscillator 23 may be separated from the pneumatic unit 9 that is responsible for the delivery of normal breaths to the patient 3. However, in other embodiments, the components of the pneumatic unit 9 may constitute the oscillator 23 and be configured to both supply the normal breaths to the patient, and to superimpose the high frequency oscillation onto the normal breaths. An example of a pneumatic unit capable of providing this dual functionality is disclosed in the co-pending application PCT/SE2012/051003, which was not public at the effective date of filing of this application. In PCT/SE2012/051003 there is disclosed a valve arrangement capable of supplying normal breaths to a patient while superimposing thereon a high frequency oscillation.

Figure 2:
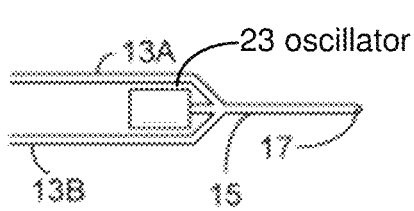
FIG. 2 illustrates an alternative location of a high frequency oscillation arrangement of the ventilation system illustrated in FIG. 1.

FIG. 2 shows an alternative location of the oscillator arrangement 23, wherein the oscillator arrangement is connected to the Y-piece of the patient circuit. Both in FIG. 1 and FIG. 2, the oscillator arrangement 23 may, for example, have a piston that is reciprocally movable within an oscillator housing by a bidirectional motor, similar to the oscillator arrangement in EP 1106197.

Figure 3:
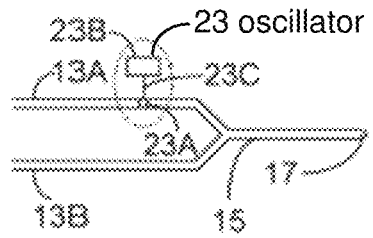
FIG. 3 illustrates yet an alternative location and design of the high frequency oscillation arrangement of the ventilation systems illustrated in FIGS. 1 and 2.

FIG. 3 shows yet an alternative location and design of the oscillator 23. Here, the oscillator 23 has a disc 23A that is arranged within the inspiratory line 13A and caused to rotate by a motor 23B to which the disc is connected through a shaft 23C, similar to the oscillator in US 2008/0245366.

The oscillator 23 of the ventilation system 1 may be a piston oscillator, a pneumatic oscillator, an electromagnetic oscillator (e.g. a loudspeaker), a so called jet or jet venturi system or any other device known in the art for generating high frequency pressure variations in a flow of breathing gas supplied to a patient. More oscillator arrangements for providing HFV to a patient are disclosed in U.S. Pat. Nos. 4,719,910, 4,805,612, 6,085,746, 7,770,580, WO 2011/031428, and EP 0512285.

The oscillator 23 is configured to apply high frequency pressure oscillations to the breaths delivered to the patient 3 by the ventilator 4 in response to the detected EMG signals. Thereby, the present invention presents a novel ventilation mode wherein HFV is combined with NAVA/EMG controlled ventilation by providing high frequency pressure oscillations that are superimposed onto an EMG controlled flow of breathing gas. This combined ventilation mode of NAVA/EMG controlled ventilation and HFV is herein referred to as HFNAVA.

Preferably but not necessarily, the oscillator 23 is controlled by the control computer 11 of the ventilator 4. In this way, the control computer 11 can control both the delivery of normal (low frequency, large tidal) breaths to the patient 3 based on the EMG signals from the EMG detector 19, and the characteristics of the HFV that is superimposed onto the normal breaths. For example, the control computer 11 may in this instance be configured to control the frequency, mean airway pressure (MAP), and the pressure amplitude of the HFV based on input from an operator of the ventilator 4. The control computer 11 may further be configured to control the pneumatic unit 9 of the ventilator 4 based on both the EMG signals detected by the EMG detector 19 and input setting parameters for the HFV in order to ensure that the effect of the combined NAVA and HFV fulfils the respiratory needs of the patient, as indicated by the detected EMG signals.

The main advantage with the ventilation system 1 and the proposed HFNAVA ventilation mode is the capability of providing improved assisted support of a spontaneous breathing effort during HFV. The control computer 11 is configured to identify when and to what extent the patient 3 wants to inhale and exhale based on the detected EMG signals, and to control the pneumatic unit 9 so as to deliver breathing gas to the patient in accordance therewith. The general concept of delivering breathing gas to the patient upon detection of a spontaneous breathing effort is often referred to as patient-triggered support ventilation since the patient's spontaneous efforts to inhale triggers the ventilator to support the efforts by delivering the breathing gas when asked for. In contrast to prior art systems offering pneumatic triggering of support ventilation during ongoing HFV, the ventilation system 1 uses neural triggering of the support ventilation. This is advantageous since the high frequency pressure oscillations of the HFV makes pneumatic triggering imprecise or even impossible.

Another advantage with the proposed ventilation system 1 is that it can be operated in many different modes of operation. The control computer 11 may, based on operator input to the ventilator 4, control the pneumatic unit 9 and the oscillator 23 such that the ventilation system 1 is operated in any ventilation mode selected from NAVA mode (EMG controlled mode), HFV mode or the above described HFNAVA mode. Furthermore, in similarity with known NAVA ventilators, the ventilation system 1 is preferably capable of operating also in conventional mechanical ventilation modes, such as pressure-controlled ventilation (PCV), volume-controlled ventilation (VCV), pressure support ventilation (PSV) and volume support ventilation (VSV). The ventilation system 1 may also be configured in accordance with the ventilator system disclosed in EP 1106197 so as to be able to offer pneumatic triggering during ongoing HFV ventilation should the EMG signal be lost.

Although modifications and changes may be suggested by those skilled in the art, it is the intention of the inventors to embody within the patent warranted hereon all changes and modifications as reasonably and properly come within the scope of their contribution to the art.

We claim as our invention:

1. A ventilation system for providing patient-triggered support ventilation to a spontaneously breathing patient during ongoing high frequency ventilation (HFV), comprising:
    a ventilator that delivers breathing gas to the spontaneously breathing patient in response to efforts to breathe by the patient;
    a control computer configured to control the delivery of breathing gas by said ventilator;
    an oscillator that superimposes high frequency oscillation onto said breathing gas so as to produce said HFV for the patient; and
    a bioelectric sensor that measures a bioelectric signal indicative of the patient's efforts to breathe,
    wherein said control computer is configured to determine neural triggering based on said bioelectric signal, and control the delivery of breathing gas by said ventilator during said HFV in response to the patient's efforts to breathe and using the neural triggering.

2. The ventilation system according to claim 1, wherein the bioelectric signal is an electromyographic (EMG) signal and the bioelectric sensor is an EMG detector.

3. The ventilation system according to claim 2, wherein the EMG detector is an oesophageal catheter comprising a plurality of electrodes for measuring EMG signals.

4. The ventilation system according to claim 1, wherein the control computer is configured to control both the ventilator and the oscillator.

5. The ventilation system according to claim 4, wherein the control computer is configured to control the delivery of breathing gas by the ventilator and the high frequency oscillation provided by the oscillator in dependence of each other, to provide an overall ventilation of the patient that fulfils respiratory needs of the patient, as indicated by the bioelectric signal.

6. The ventilation system according to claim 1, wherein the ventilator is configured to provide neurally adjusted ventilatory assist (NAVA), based on the bioelectric signal measured by the bioelectric sensor.

7. The ventilation system according to claim 6, wherein the oscillator is integrated in the ventilator.

8. The ventilation system according to claim 1, wherein the control computer is configured to control the ventilator and the oscillator to selectively operate the ventilation system in a ventilation mode selected from:
    only a neurally adjusted ventilatory assist (NAVA) mode,
    only an HFV mode, and
    a ventilation mode combining NAVA and HFV by superimposing high frequency oscillation onto neurally adjusted ventilation that is provided to the patient based on said bioelectric signal.

9. The ventilation system according to claim 1, wherein said EMG detector is an oesophageal catheter.

10. A ventilation system for providing patient-triggered support ventilation to a spontaneously breathing patient during ongoing high frequency ventilation (HFV), comprising:
    a ventilator that delivers breathing gas to the patient in response to efforts to breathe by the patient;
    a control computer configured to control the delivery of breathing gas by the ventilator;
    an oscillator that superimposes high frequency oscillation onto said breathing gas so as to produce said HFV for the patient; and
    said control computer being configured to control both the ventilator and the oscillator so as to control the delivery of said breathing gas with neural triggering in response to the patient's efforts to breathe during said HFV as indicated by a bioelectric signal, and to adjust said high frequency oscillation produced by said oscillator, so that the delivery of said breathing gas by the ventilator and the high frequency oscillation provided by said oscillator are controlled by the control computer in dependence on each other so as to provide HFV for the patient that fulfils respiratory needs of the patient as indicated by the bioelectric signal.

* * * * *